United States Patent
Douezan et al.

(10) Patent No.: US 10,493,015 B2
(45) Date of Patent: Dec. 3, 2019

(54) COSMETIC COMPOSITION FOR COATING KERATIN FIBRES

(71) Applicant: L'OREAL, Paris (FR)

(72) Inventors: Stephane Douezan, Le Kremlin Bicetre (FR); Philippe Ilekti, Maisons-Alfort (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/303,181

(22) PCT Filed: Apr. 9, 2015

(86) PCT No.: PCT/EP2015/057752
§ 371 (c)(1),
(2) Date: Oct. 10, 2016

(87) PCT Pub. No.: WO2015/155302
PCT Pub. Date: Oct. 15, 2015

(65) Prior Publication Data
US 2017/0112753 A1 Apr. 27, 2017

(30) Foreign Application Priority Data
Apr. 11, 2014 (FR) ..................... 14 53264

(51) Int. Cl.
| | | |
|---|---|---|
| *A61K 8/86* | (2006.01) | |
| *A61K 8/19* | (2006.01) | |
| *A61K 8/02* | (2006.01) | |
| *A61K 8/39* | (2006.01) | |
| *A61Q 1/10* | (2006.01) | |

(52) U.S. Cl.
CPC .............. *A61K 8/86* (2013.01); *A61K 8/0295* (2013.01); *A61K 8/19* (2013.01); *A61K 8/39* (2013.01); *A61Q 1/10* (2013.01); *A61K 2800/43* (2013.01); *A61K 2800/594* (2013.01)

(58) Field of Classification Search
None
See application file for complete search history.

(56) References Cited

U.S. PATENT DOCUMENTS

2005/0172421 A1* 8/2005 Jager-Lezer .......... A61K 8/731
    8/405
2009/0016982 A1 1/2009 Raineau et al.

FOREIGN PATENT DOCUMENTS

| FR | 2 833 163 A1 | 6/2003 | |
|---|---|---|---|
| FR | 2 908 307 A1 | 5/2008 | |
| JP | 11-79940 * | 3/1999 | ............. A61K 7/032 |
| JP | 2008-120817 A | 5/2008 | |
| WO | 2014/060310 A1 | 4/2014 | |

OTHER PUBLICATIONS

Machine translation, FR 2833163 (2003).*
Machine translation, JP 11-79940 (1999).*
"Personal Care; Pluracare L/F Grades Poloxamer; Technical Information", Registered trademark of BASF group, pp. 1-10, (Jul. 2009), XP055118205.
International Search Report dated Jul. 6, 2015 in PCT/EP15/057752 Filed Apr. 9, 2015.

* cited by examiner

*Primary Examiner* — Bethany P Barham
*Assistant Examiner* — Barbara S Frazier
(74) *Attorney, Agent, or Firm* — Oblon, McClelland, Maier & Neustadt, L.L.P.

(57) ABSTRACT

The present invention relates to a composition, preferably a cosmetic composition, in particular for coating keratin fibres such as the eyelashes, comprising: —an aqueous phase, —a lamellar phase Lβ formed by an aqueous phase-structuring surfactant system, said surfactant system comprising a content of surfactant(s) of greater than or equal to 15% by weight relative to the total weight of the composition, —at least one (poly)oxyalkylenated hydrophilic polymer present in a content of greater than or equal to 3% by weight of solids relative to the total weight of the composition, the hydrophilic polymer(s) having a weight-average molecular mass Mw ranging from 1500 to 500 000 g/mol. The present invention also relates to a process for coating keratin fibres.

11 Claims, No Drawings

COSMETIC COMPOSITION FOR COATING KERATIN FIBRES

The present invention relates to a cosmetic composition for coating keratin fibres, and in particular the eyelashes or the eyebrows. In particular, said cosmetic composition is a composition for making up and optionally caring for the eyelashes. The present invention also relates to a process for coating keratin fibres, in particular a process for making up and optionally caring for the eyelashes. The present invention also relates to particular uses.

The composition used may in particular be in the form of an eyelash product such as a mascara, or an eyebrow product. More preferentially, the invention relates to a mascara. The term "mascara" is intended to mean a composition intended to be applied to the eyelashes: it may be an eyelash makeup composition, an eyelash makeup base (also known as a base coat), a composition to be applied over a mascara, also known as a top coat, or else a cosmetic composition for treating the eyelashes. The mascara is more particularly intended for human eyelashes, but also false eyelashes.

Mascaras are in particular prepared according to two types of formulation: water-based mascaras known as cream mascaras, in the form of a dispersion of waxes in water; anhydrous mascaras or mascaras with a low water content, known as waterproof mascaras, in the form of dispersions of waxes in organic solvents.

Generally, anhydrous mascaras have good water resistance, but the level of volume is generally low and the makeup removal is difficult, whereas water-based mascaras have lower water resistance but a high level of volume and easier makeup removal.

The present patent application more specifically relates to what is known as water-based mascaras.

Keratin fibre coating compositions of such a mascara type generally consist of at least one fatty phase generally formed from one or more waxes dispersed in an aqueous liquid phase by means of an emulsifying system or conveyed in an organic solvent.

The presence of wax(es) is known to provide a good texture capable of charging the eyelashes to give them a volume effect, but has the drawback of reducing the colour intensity of the composition. Moreover, reducing the amount of waxes produces solutions whose colour intensity is high, but the composition thus fluidized gives rise to a makeup that charges sparingly.

One aim of the present invention is to obtain a composition for coating keratin fibres, preferably a mascara, which gives a charging effect on the eyelashes while at the same time having good colour intensity, in particular good black intensity, and having good properties in terms of shaping of the curl of the eyelashes with a pleasant application. Hard waxes are known to provide a curling effect, but, at high concentration, they are relatively unpleasant to apply since the texture is rigid.

An aim of the present patent application is also to propose a stable mascara, which has a texture that is thick enough to obtain a charging deposit, of satisfactory consistency, allowing easy application to the eyelashes and uniform deposition, i.e. smooth and homogeneous, even after two months stored at 4° C.

An aim of the present patent application is also to propose a stable mascara, which has a texture that is thick enough to obtain a charging deposit, of satisfactory consistency, allowing easy application to the eyelashes and uniform deposition, i.e. smooth and homogeneous, even after two months stored at 45° C.

An aim of the present patent application is more particularly to propose a stable mascara, which has a texture that is thick enough to obtain a charging deposit, of satisfactory consistency, allowing easy application to the eyelashes and uniform deposition, i.e. smooth and homogeneous, even after two months stored at temperatures oscillating between 4° C. and 45° C.

More particularly, an aim of the present invention consists in stabilizing a mascara without phase separation over time.

An aim of the present patent application is more particularly to propose a mascara in which the pigments are uniformly dispersed.

An aim of the present patent application is more particularly to propose a mascara that is pleasant to apply.

An aim of the present invention is more particularly to propose a composition for coating keratin fibres that allows good separation of the eyelashes during its application, without formation of bunches of eyelashes, and while ensuring smooth and uniform deposition of material (without lumps of composition).

An aim of the present invention is also to obtain a composition for coating keratin fibres, preferably a mascara, which has good staying power on the eyelashes.

Consequently, one subject of the present invention is a composition, preferably a cosmetic composition, in particular for coating keratin fibres such as the eyelashes, comprising:
  an aqueous phase,
  a lamellar phase Lβ formed by an aqueous phase-structuring surfactant system, said surfactant system comprising a content of surfactant(s) of greater than or equal to 15% by weight relative to the total weight of the composition,
  at least one (poly)oxyalkylenated hydrophilic polymer present in a content of greater than or equal to 1% by weight of solids relative to the total weight of the composition, the hydrophilic polymer(s) having a weight-average molecular mass Mw ranging from 1500 to 500 000 g/mol.

Surprisingly and unexpectedly, the inventors of the present patent application have succeeded in formulating compositions, which are especially suitable for coating keratin fibres such as the eyelashes, in particular a mascara composition, which is capable of considerably limiting or even capable of dispensing with the use of waxes.

In particular, a composition in accordance with the invention gives rise to a composition that is stable even after 2 months whether at 45° C. or at 4° C. It appears that such a composition is smooth, glossy and has an intense black colour. Such a composition is also pleasant to apply, comfortable and has a very good playtime. Furthermore, this composition promotes shaping of the curl of the eyelashes, the inventors putting forward the hypothesis that the hydrophilic polymer(s) selected give the composition a desiccating and rigidifying effect.

Furthermore, when combined with a high wax content, for example greater than or equal to 10% by weight, and more surprisingly with a high content of hard wax(es), for example greater than or equal to 10% by weight, the present invention makes it possible to conserve comfort on application and in particular unexpected playtime, allowing more than 20 brushstrokes on the eyelashes without the user sensing any dragging.

According to a second aspect, a subject of the present invention is also an assembly or kit for coating keratin fibres, comprising:

at least one cosmetic composition for coating keratin fibres as described previously, and at least one applicator for the composition, said applicator comprising means, where appropriate with reliefs, configured to come into contact with said keratin fibres, such as the eyelashes or the eyebrows, so as to smooth and/or separate the eyelashes or the eyebrows. Such reliefs may comprise teeth, bristles or the like. Said assembly, and in particular said applicator, may optionally be equipped with means for vibrating and/or heating said composition.

According to a third aspect, a subject of the present invention is also an assembly or kit for packaging and applying a composition for coating keratin fibres, comprising:

a device for packaging said cosmetic composition for coating keratin fibres as described previously, an applicator for said composition.

Said applicator may be integrally attached to a gripping member forming a cap for said packaging device. In other words, said applicator may be mounted in a removable position on said device between a closed position and an open position of a dispensing aperture of the device for conditioning said composition.

According to particular preferred embodiments of the present invention concerning the compositions and processes described above and directed towards solving at least one of the abovementioned problems:

the surfactant system comprises at least one nonionic surfactant; preferably, the surfactant system comprises a total content of nonionic surfactant(s) of greater than or equal to 15% by weight relative to the total weight of the composition;

the surfactant system comprises a total content of surfactant(s), preferably of nonionic surfactant(s), of greater than or equal to 18% by weight, in particular 20% by weight, for example ranging from 15% to 45% by weight, better still from 18% to 40% by weight and even better still from 20% to 35% by weight relative to the total weight of the composition;

the surfactant system comprises:
at least one nonionic surfactant with an HLB value at 25° C. of less than 8, and
at least one nonionic surfactant with an HLB value at 25° C. of greater than or equal to 8;
the nonionic surfactant(s) with an HLB value at 25° C. of greater than or equal to 8 and less than or equal to 8 correspond to formula (I) below:

$$(ALK-[C(O)]_a\text{—}[O]_b)_c\text{—}X \qquad (I)$$

in which formula (I):
ALK is a $C_7$-$C_{23}$, preferably $C_{11}$-$C_{21}$ and more preferentially $C_{15}$-$C_{17}$ alkyl group,
a and b are integers between 0 and 100, c is an integer between 1 and 100, in particular between 1 and 3, preferably equal to 1, a and b preferably being equal to 0 or 1,
X is a (poly)oxyalkylene group optionally substituted and/or terminated with a hydroxyl group, X preferably being an oxyethylene group $(CH_2CH_2O)_n$ or $(OCH_2CH_2)_n$ in which n is greater than or equal to 1, for example between 1 and 200, said (poly)oxyalkylene group preferably being a polyethylene glycol or being the result of at least one substitution of a hydroxyl group, preferably chosen from (poly)glycerols;
The group X is preferably chosen from:

$$HO\text{-}(ALK\text{-}O)_z\text{—}CH2\text{-}CH[(OALK)_y\text{-}OH]\text{—}CH2\text{-}(O\text{-}ALK)_x\text{-}(*) \qquad i)$$

in which:
ALK, which may be identical or different, representing a C1-C6 and in particular C1-C4 alkylene group, preferably ethylene,
x, y and z being an integer between 0 and 200, it being understood that x+y+z is other than 0, x+y+z preferably being inclusively between 1 and 150 and in particular between 20 and 60;

$$H\text{-}(ALK\text{-}O)_x\text{-}(*) \text{ and } H\text{—}(O\text{-}ALK)_x\text{-}(*), \text{ preferably is } H\text{—}(O\text{-}ALK)_x\text{-}(*) \qquad ii)$$

in which:
ALK, which may be identical or different, representing a C1-C6 and in particular C1-C4 ethylene group, preferably ethylene,
x is an integer other than 0 and preferably between 1 and 200.

at least one from among the nonionic surfactant(s) with an HLB value at 25° C. of less than 8 and the nonionic surfactant(s) with an HLB value at 25° C. of greater than or equal to 8, preferably the nonionic surfactant(s) with an HLB value at 25° C. of less than 8 and the nonionic surfactant(s) with an HLB value at 25° C. of greater than or equal to 8, are chosen from:

those corresponding to formula (I') below:

$$ALK\text{-}(O\text{—}CH_2\text{—}CH_2)_n\text{—}OH \qquad (I')$$

in which formula (I'):
ALK is a $C_8$-$C_{24}$, preferably $C_{12}$-$C_{22}$ and more preferentially $C_{16}$-$C_{18}$ alkyl group,
n being an integer other than 0, between 1 and 200, preferably between 1 and 10 and better still between 2 and 6 for the nonionic surfactant(s) with an HLB value at 25° C. of less than 8, preferably between 20 and 200 for the nonionic surfactant(s) with an HLB value at 25° C. of greater than or equal to 8;

those corresponding to formula (I") below:

$$(ALK\text{-}[C(O)]_a\text{—}[O]_b)_c\text{-}(Gly)_d \qquad (I'')$$

in which formula (I"):
ALK is a $C_7$-$C_{23}$, preferably $C_{11}$-$C_{21}$ and more preferentially $C_{15}$-$C_{17}$ alkyl group,
a and b are integers between 0 and 100, c is an integer between 1 and 100, in particular between 1 and 3, preferably equal to 1, a and b preferably being equal to 0 or 1,
Gly is a glycerol group, optionally substituted and/or terminated with a hydroxyl group, in particular in which at least one of the —OH functions, and preferentially only one —OH function, is substituted with the group $(ALK\text{-}[C(O)]_a\text{—}[O]_b)_c$, preferentially ALK-(CO)—O,
d is an integer between 1 and 20, preferably between 1 and 12, preferably being between 1 and 2 for the nonionic surfactant(s) with an HLB value at 25° C. of less than 8, and between 4 and 20 for the nonionic surfactant(s) with an HLB value at 25° C. of greater than or equal to 8;
and a mixture thereof;

the at least one from among the nonionic surfactant(s) with an HLB value at 25° C. of less than 8 is chosen from:
(poly)oxyalkylenated monosaccharide esters and ethers; esters of fatty acids, especially of $C_8$-$C_{24}$ and preferably of $C_{16}$-$C_{22}$, and of (poly)oxyalkylenated polyol, especially of (poly)oxyalkylenated glycerol or of oxyalkylenated sorbitol, preferably of (poly)oxyalkylenated glycerol;

esters of fatty acids, especially of $C_8$-$C_{24}$ and preferably of $C_{16}$-$C_{22}$, and of (poly)glycerol, preferentially comprising one or two glycerol groups;

(poly)oxyalkylenated alcohols;

and mixtures thereof, preferably from (poly)oxyalkylenated alcohols;

the at least one from among the nonionic surfactant(s) with an HLB value at 25° C. of less than 8 comprises a (poly)oxyalkylenated alcohol comprising an ether of a $C_8$-$C_{24}$ fatty alcohol and of polyethylene glycol, said ether comprising from 1 to 10 and better still between 2 and 6 ethylene glycol units;

the nonionic surfactant(s) with an HLB value at 25° C. of greater than or equal to 8, preferably greater than or equal to 10, are chosen from:

(poly)oxyalkylenated glycerol ethers, (poly)oxyalkylenated alcohols, esters of a fatty acid and of (poly)oxyalkylenated polyethylene glycol, esters of a fatty acid and of (poly)oxyalkylenated glycerol ethers, esters of fatty acids, especially of $C_8$-$C_{24}$ and preferably of $C_{16}$-$C_{22}$, and of polyglycerol, preferentially comprising from 4 to 20 glycerol groups;

esters of a fatty acid and of (poly)oxyalkylenated sorbitol ethers, and mixtures thereof; preferably from (poly)oxyalkylenated alcohols;

the at least one from among the nonionic surfactant(s) with an HLB value at 25° C. of greater than or equal to 8 comprises a (poly)oxyalkylenated alcohol comprising at least one ether of a $C_8$-$C_{24}$ fatty alcohol and of polyethylene glycol, said ether comprising at least 20 ethylene glycol units and better still between 20 and 200 ethylene glycol units;

the nonionic surfactant(s) with an HLB value at 25° C. of less than 8, preferably corresponding to formula (I), are present in a content of greater than or equal to 7% by weight relative to the total weight of the composition, preferably between 8% and 25% by weight relative to the total weight of the composition;

the nonionic surfactant(s) with an HLB value at 25° C. of greater than or equal to 8, preferably greater than or equal to 10, preferably corresponding to formula (I), are present in a content of greater than or equal to 7% by weight relative to the total weight of the composition, preferably between 8% and 25% by weight relative to the total weight of the composition;

the nonionic surfactant(s) with an HLB value at 25° C. of less than 8, and the nonionic surfactant(s) with an HLB value at 25° C. of greater than or equal to 8, preferably both corresponding to formula (I), are present in a total content of greater than or equal to 15%, better still 18%, in particular between 15% and 45%, better still from 18% to 40% by weight and even better still from 20% to 35% by weight relative to the total weight of the composition;

the nonionic surfactant(s) with an HLB value at 25° C. of less than 8 and the nonionic surfactant(s) with an HLB value at 25° C. of greater than or equal to 8, both preferably corresponding to formula (I), are present in a respective total content such that the weight ratio of the nonionic surfactant(s) with an HLB value at 25° C. of less than 8 to the nonionic surfactant(s) with an HLB value at 25° C. of greater than or equal to 8 ranges from 1/5 to 5, preferably from 1/3 to 3, preferably from 2/3 to 3/2;

said composition comprises a solids content of greater than or equal to 40%, better still 42%, preferentially 45%, more preferentially 48%, or even 50%;

the aqueous phase represents from 30% to 80% by weight and preferably from 40% to 70% by weight relative to the total weight of the composition;

the hydrophilic polymer(s) are linear;

the hydrophilic polymer(s) are chosen from statistical polymers, block copolymers, and a mixture thereof;

the hydrophilic polymer(s) are chosen from:

(poly)oxyalkylenated homopolymers, in particular polyoxyalkylenated homopolymers, more particularly polyethylene glycol homopolymers, (poly)oxyalkylenated copolymers, in particular (poly)propylene glycol/(poly) ethylene glycol copolymers, in particular polypropylene glycol/polyethylene glycol copolymers, (poly)oxyalkylenated block copolymers, in particular (poly)oxyalkylenated diblock or triblock copolymers, more particularly diblock or triblock copolymers of (poly)ethylene glycol and of (poly)propylene glycol, even more particularly diblock or triblock copolymers of polyethylene glycol and of polypropylene glycol, and a mixture thereof;

the hydrophilic polymer(s) bearing a (poly)oxyalkylene unit comprise from 35 to 10 000 oxyethylene units, in particular from 35 to 5000 oxyethylene units and even more preferentially from 40 to 2500 oxyethylene units;

said composition comprises from 0 to 25% of fatty phase relative to the total weight of the composition and more preferentially from 1% to 15% by weight relative to the total weight of the composition;

the composition comprises from 0 to 25% by weight of wax(es), in particular from 0.5% to 15% or even from 1% to 8% by weight of wax(es);

the composition comprises a content of wax(es) of less than 5% by weight, in particular 3% by weight and preferentially 1% by weight relative to the total weight of the composition;

the composition comprises at least one wax chosen from the group consisting of polar waxes and apolar waxes, and a mixture thereof;

the composition comprises at least one polar wax;

the composition comprises at least one hard wax, which is preferably polar;

the composition comprises less than 5% by weight of wax(es), preferably hard wax(es), which are preferably polar, and at least 3% by weight of (poly)oxyalkylenated hydrophilic polymer(s), relative to the total weight of the composition; more particularly, the composition comprises less than 3% by weight of wax(es), preferably hard wax(es), which are preferably polar, and at least 5% by weight of (poly)oxyalkylenated hydrophilic polymer(s), relative to the total weight of the composition, and even more particularly the composition comprises less than 1% by weight of wax(es), preferably hard wax(es), which are preferably polar, and at least 8% by weight of (poly)oxyalkylenated hydrophilic polymer(s), relative to the total weight of the composition;

the composition comprises at least 10% by weight of wax(es), preferably hard wax(es), which are preferably polar, and at least 1% by weight of (poly)oxyalkylenated hydrophilic polymer(s), relative to the total weight of the composition; in particular, the composition comprises at least 12% by weight of hard wax(es), which are preferably polar, and at least 1% by weight of (poly)oxyalkylenated hydrophilic polymer(s), relative to the total weight of the composition, and more particularly the composition comprises at least 15% by weight of hard wax(es), which are preferably polar, and at least 1% by weight of (poly)oxyalkylenated hydrophilic polymer(s), relative to the total weight of the composition;

said composition is free of oil or organic solvent;

said composition comprises at least one film-forming polymer present in the form of particles in dispersion, for example in aqueous dispersion;

the total content of film-forming polymer particles present in aqueous dispersion form ranges from 0 to 20% by weight and preferably from 0 to 5% by weight relative to the total weight of the composition;

said composition comprises at least one dyestuff chosen from one or more pulverulent substance(s), preferably metal oxides, and in particular iron oxides;

the metal oxide(s) are preferably present in a content of greater than or equal to 2% by weight relative to the total weight of the composition, and advantageously inclusively between 3% and 22% by weight relative to the total weight of the composition;

said composition has a viscosity at 25° C. ranging from 5 to 50 Pa·s, in particular measured using a Rheomat RM100® machine;

said composition may be a makeup composition, a makeup base or "base coat", or a "top coat" composition to be applied onto a makeup.

Other characteristics, properties and advantages of the present invention will emerge more clearly on reading the description and the examples that follow.

Throughout the description that follows, and unless otherwise mentioned:

The term "(poly)oxyalkylene" or "(poly)oxyalkylenated" means that one or more —OH functions, in particular derived from a hydroxyl function or a carboxylic function, may be substituted with an oxyalkylene group, in particular an oxyethylene group.

The term "acyl" means a linear or branched saturated $C_8$-$C_{24}$, better still $C_{12}$-$C_{20}$ and more preferentially $C_{14}$-$C_{18}$ hydrocarbon-based chain comprising a carboxylic function whose hydroxyl function (—OH) has been substituted.

An "alkyl" group is a linear or branched, preferably linear, $C_7$-$C_{23}$, preferably $C_{11}$-$C_{21}$ and more preferentially $C_{15}$-$C_{17}$ hydrocarbon-based group or chain.

The "hydrocarbon-based chain" is optionally "(poly)unsaturated" when it comprises one or more double bonds and/or one or more triple bonds, which may be conjugated or non-conjugated; preferably, this hydrocarbon-based chain is saturated.

Aqueous Phase

The composition according to the invention comprises an aqueous phase, which may form a continuous phase of the composition.

The aqueous phase comprises water. It may also comprise at least one water-soluble solvent.

In the present invention, the term "water-soluble solvent" denotes a compound that is liquid at room temperature and water-miscible.

The water-soluble solvents that may be used in the compositions according to the invention may also be volatile.

Among the water-soluble solvents that may be used in the compositions in accordance with the invention, mention may be made in particular of lower monoalcohols containing from 1 to 5 carbon atoms such as ethanol and isopropanol, and glycols containing from 2 to 8 carbon atoms such as ethylene glycol, propylene glycol, 1,3-butylene glycol and dipropylene glycol.

The aqueous phase (water and optionally the water-miscible solvent) is generally present in the composition according to the present patent application in a content ranging from 30% to 80% by weight relative to the total weight of the composition, and preferably ranging from 40% to 70% by weight relative to the total weight of the composition. This aqueous phase content includes not only the water originating from the aqueous dispersions of film-forming polymers, and, where appropriate, aqueous dispersions of hard waxes, in accordance with the invention, but also, where appropriate, the water deliberately added to the composition.

Solids Content

The composition according to the invention advantageously comprises a solids content of greater than or equal to 40%, better still 42%, in particular 45%, or even 48%, and preferentially 50%.

For the purposes of the present invention, the "solids content" denotes the content of non-volatile matter.

The solids content (abbreviated as SC) of a composition according to the invention is measured using a "Halogen Moisture Analyzer HR 73" commercial halogen desiccator from Mettler Toledo. The measurement is performed on the basis of the weight loss of a sample dried by halogen heating, and thus represents the percentage of residual matter once the water and the volatile matter have evaporated off.

This technique is fully described in the machine documentation supplied by Mettler Toledo.

The measuring protocol is as follows:

Approximately 2 g of the composition, referred to hereinbelow as the sample, are spread out on a metal crucible, which is placed in the halogen desiccator mentioned above. The sample is then subjected to a temperature of 105° C. until a constant weight is obtained. The wet mass of the sample, corresponding to its initial mass, and the dry mass of the sample, corresponding to its mass after halogen heating, are measured using a precision balance.

The experimental error associated with the measurement is of the order of plus or minus 2%.

The solids content is calculated in the following manner:

$$\text{Solids content (expressed as weight percentage)} = 100 \times (\text{dry mass/wet mass}).$$

Surfactant System

A composition in accordance with the invention comprises a surfactant system forming a lamellar phase LR in the aqueous phase.

This surfactant system structuring the aqueous phase in a lamellar phase Lβ comprises a content of surfactant(s), preferably nonionic surfactant(s), of greater than or equal to 15% by weight relative to the total weight of the composition.

The surfactant system advantageously comprises a total content of surfactant(s), preferably of nonionic surfactant(s), of greater than or equal to 15% by weight, in particular 18% by weight, more particularly ranging from 15% to 45% by weight, better still from 18% to 40% by weight and even better still from 20% to 35% by weight relative to the total weight of the composition.

According to one preferred embodiment, a composition according to the invention comprises a surfactant system comprising:

at least one nonionic surfactant with an HLB value at 25° C. of less than 8, and at least one nonionic surfactant with an HLB value at 25° C. of greater than or equal to 8, at least one from among the nonionic surfactant(s) with an HLB value at 25° C. of less than 8 and at least one from among the nonionic surfactant(s) with an HLB value at 25° C. of greater than or equal to 8 corresponding to formula (I) below:

$$(ALK-[C(O)]_a—[O]_b)_c—X—(I)$$

in which formula (I):
- ALK is a $C_7$-$C_{23}$, preferably $C_{11}$-$C_{21}$ and more preferentially $C_{15}$-$C_{17}$ alkyl group,
- a and b are integers between 0 and 100, c is an integer between 1 and 100, in particular between 1 and 3, preferably equal to 1, a and b preferably being equal to 0 or 1,
- X is a (poly)oxyalkylene group optionally substituted and/or terminated with a hydroxyl group, X preferably being an oxyethylene group $(CH_2CH_2O)_n$ or $(OCH_2CH_2)_n$ in which n is greater than or equal to 1, for example between 1 and 200, said (poly)oxyalkylene group preferably being a polyethylene glycol or being the result of at least one substitution of a hydroxyl group, preferably chosen from (poly)glycerols.

In particular:

$ALK-[C(O)]_a—[O]_b$ generally means that the alkyl group ALK may be derived from a fatty acid or from a fatty alcohol.

$[C(O)]_a—[O]_b$ means that the ALK group may comprise at least one function chosen from an ester function COO (when a+b=1), a carbonyl function CO (when a=1 and b=0), an oxy function O (when a=0 and b=1), or may be directly linked to the oxyalkylene group (when a+b=0).

The compounds of formula (I) preferably result from an esterification, more preferentially from a mono esterification, or from an etherification (or alkoxylation), more preferentially a mono-etherification (or mono-alkoxylation).

The group X is preferably chosen from:

$$HO\text{-}(ALK\text{-}O)_z—CH2\text{-}CH[(OALK)_y\text{-}OH]—CH2\text{-}(O\text{-}ALK)_x\text{-}(*) \quad \text{i)}$$

in which:
- ALK, which may be identical or different, representing a C1-C6 and in particular C1-C4 alkylene group, preferably ethylene,
- x, y and z being an integer between 0 and 200, it being understood that x+y+z is other than 0, x+y+z preferably being inclusively between 1 and 150 and in particular between 20 and 60;

$$H\text{-}(ALK\text{-}O)_x\text{-}(*) \text{ and } H—(O\text{-}ALK)_x\text{-}(*), \text{ preferably is } H—(O\text{-}ALK)_x\text{-}(*) \quad \text{ii)}$$

in which:
- ALK, which may be identical or different, representing a C1-C6 and in particular C1-C4 ethylene group, preferably ethylene,
- x is an integer other than 0 and preferably between 1 and 200.

According to a particularly preferred embodiment, the nonionic surfactant(s) with an HLB value at 25° C. of less than 8 and the nonionic surfactant(s) with an HLB value at 25° C. of greater than or equal to 8 are chosen from:
- those corresponding to formula (I') below:

$$ALK\text{-}(O—CH_2—CH_2)_n—OH \quad (I')$$

in which formula (I'):
- ALK is a $C_8$-$C_{24}$, preferably $C_{12}$-$C_{22}$ and more preferentially $C_{16}$-$C_{18}$ alkyl group,
- n being an integer other than 0, between 1 and 200, preferably between 1 and 10 and better still between 2 and 6 for the nonionic surfactant(s) with an HLB value at 25° C. of less than 8, preferably between 20 and 200 for the nonionic surfactant(s) with an HLB value at 25° C. of greater than or equal to 8;

those corresponding to formula (I") below:

$$(ALK\text{-}[C(O)]_a—[O]_b)_c\text{-}(Gly)_d \quad (I")$$

in which formula (I"):
- ALK is a $C_7$-$C_{23}$, preferably $C_{11}$-$C_{21}$ and more preferentially $C_{15}$-$C_{17}$ alkyl group,
- a and b are integers between 0 and 100, c is an integer between 1 and 100, in particular between 1 and 3, preferably equal to 1, a and b preferably being equal to 0 or 1,
- Gly is a glycerol group, optionally substituted and/or terminated with a hydroxyl group, in particular in which at least one of the —OH functions, and preferentially only one —OH function, is substituted with the group $(ALK\text{-}[C(O)]_a—[O]_b)_c$, preferentially ALK-(CO)—O,
- d is an integer between 1 and 20, preferably between 1 and 12, preferably being between 1 and 2 for the nonionic surfactant(s) with an HLB value at 25° C. of less than 8, and between 4 and 20 for the nonionic surfactant(s) with an HLB value at 25° C. of greater than or equal to 8;

and a mixture thereof.

The Griffin HLB (hydrophilic/lipophilic balance) value is defined in J. Soc. Cosm. Chem. 1954 (volume 5), pages 249-256. Reference may be made to the Kirk-Othmer Encyclopedia of Chemical Technology, volume 22, p. 333-432, 3rd edition, 1979, Wiley, for the definition of the properties and functions of surfactants, in particular p. 347-377 of this reference.

Nonionic Surfactant(s) with an HLB Value at 25° C. of Greater than or Equal to 8

The nonionic surfactant(s) with an HLB value, in the Griffin sense, at 25° C., of greater than or equal to 8 may be advantageously chosen from:
- (poly)oxyalkylenated glycerol ethers, in particular oxyethylenated and/or oxypropylenated glycerol ethers, which may comprise from 20 to 200 oxyethylene and/or oxypropylene units;
- (poly)oxyalkylenated alcohols, in particular oxyethylenated and/or oxypropylenated alcohols, which may comprise from 20 to 200 oxyethylene and/or oxypropylene units, preferably from 20 to 100 oxyethylene units, in particular ethoxylated fatty alcohols, especially $C_8$-$C_{24}$ and preferably $C_{12}$-$C_{18}$ fatty alcohols, such as ethoxylated stearyl alcohol comprising 20 oxyethylene units (CTFA name: Steareth-20) such as Brij 78 sold by the company Uniqema, or ethoxylated cetearyl alcohol comprising 30 oxyethylene units (CTFA name: Steareth-30);
- (poly)oxyalkylenated fatty acid esters, in particular esters of a fatty acid, especially of a $C_8$-$C_{24}$ and preferably $C_{16}$-$C_{22}$ fatty acid, and of polyethylene glycol (or PEG) (which may comprise from 20 to 200 oxyethylene units), such as PEG-50 stearate and PEG-40 monostearate sold under the name Myrj 52P® by the company Uniqema;
- esters of a fatty acid, especially a $C_8$-$C_{24}$ and preferably $C_{16}$-$C_{22}$ fatty acid, and of (poly)oxyalkylenated glycerol ethers, which are in particular oxyethylenated and/or oxypropylenated (which may comprise from 20 to 200 oxyethylene and/or oxypropylene units), for instance glyceryl monostearate polyoxyethylenated with 200 oxyethylene units, sold under the name Simulsol 220 TM® by the company SEPPIC; glyceryl stearate polyoxyethylenated with 30 oxyethylene units, for instance the product Tagat S® sold by the company Goldschmidt, glyceryl oleate polyoxyethylenated with 30 oxyethylene units, for instance the product Tagat O® sold by the company Goldschmidt, glyceryl cocoate polyoxyethylenated with 30 oxyethylene units, for instance the product Varionic LI 13® sold by the company Sherex, glyceryl isostearate polyoxyethylenated with 30 oxyethylene units, for instance the product Tagat L® sold by the company Goldschmidt, and glyceryl laurate polyoxyethylenated with 30 oxyethylene units, for instance the product Tagat I® from the company Goldschmidt;

esters of a fatty acid, especially of $C_8$-$C_{24}$ and preferably of $C_{16}$-$C_{22}$, and of a polyglycerol, preferentially comprising from 4 to 20 glycerol groups; esters of a fatty acid, especially a $C_8$-$C_{24}$ and preferably $C_{16}$-$C_{22}$ fatty acid, and of (poly)oxyalkylenated sorbitol ethers, which are in particular oxyethylenated and/or oxypropylenated (which may comprise from 20 to 200 oxyethylene and/or oxypropylene units), for instance the polysorbate 60 sold under the name Tween 60® by the company Uniqema;

and mixture(s) thereof; preferably, among the (poly)oxyalkylenated alcohols preferably comprising from 20 to 200 oxyethylene (or ethylene glycol) units.

The term "fatty acid" should preferentially be understood as meaning a fatty monoacid.

Preferably, a composition comprises at least one nonionic surfactant with an HLB value, in the Griffin sense, at 25° C., of greater than or equal to 8, preferably greater than or equal to 10, chosen from:

at least one ether of a $C_8$-$C_{24}$, preferably $C_{12}$-$C_{22}$ and more preferentially $C_{16}$-$C_{18}$ fatty alcohol and of polyethylene glycol, said ether comprising at least 20 ethylene glycol units and better still between 20 and 200 ethylene glycol units, at least one ester of a $C_{12}$-$C_{20}$ fatty acid and of a polyglycerol comprising from 4 to 20 glycerol groups, in particular from 8 to 12 glycerol groups, such as 10 glycerol groups, the alkyl chain of the fatty acid advantageously being linear or branched, and saturated or unsaturated, preferably linear and saturated, preferentially chosen from polyglyceryl-10 stearate, polyglyceryl-10 laurate, polyglyceryl-10 myristate, and a mixture thereof, preferably polyglyceryl-10 stearate, and a mixture thereof.

A composition according to the invention has a content of nonionic surfactant(s) with an HLB value in the Griffin sense, at 25° C., of greater than or equal to 8, preferably greater than or equal to 10, of greater than or equal to 7% by weight relative to the total weight of the composition, preferably between 8% and 25% by weight relative to the total weight of the composition.

Nonionic Surfactant(s) with an HLB Value at 25° C. of Less than 8 The nonionic surfactant(s) with an HLB value, in the Griffin sense, at 25° C., of less than 8 comprise at least one surfactant advantageously chosen from:

(poly)oxyalkylenated monosaccharide esters and ethers; esters of fatty acids, especially of $C_8$-$C_{24}$ and preferably of $C_{16}$-$C_{22}$, and of (poly)oxyalkylenated polyol, especially of (poly)oxyalkylenated glycerol or of (poly)oxyalkylenated sorbitol, preferably of (poly)oxyalkylenated glycerol;

esters of fatty acids, especially of $C_8$-$C_{24}$ and preferably of $C_{16}$-$C_{22}$, and of (poly)glycerol, preferentially comprising one or two glycerol groups;

(poly)oxyalkylenated alcohols;

and mixture(s) thereof; preferably from (poly)oxyalkylenated alcohols preferably comprising from 1 to 10 oxyethylene units.

The term "(poly)oxyalkylenated" means from 1 to 10 oxyethylene groups (or units) and better still from 2 to 6 oxyethylene groups.

The term "fatty acid" should preferentially be understood as meaning a fatty monoacid.

The nonionic surfactant(s) with an HLB value at 25° C. of less than 8 are preferably chosen from:

at least one (poly)oxyalkylenated alcohol comprising an ether of a $C_8$-$C_{24}$ fatty alcohol and of polyethylene glycol, said ether comprising from 1 to 10 and better still between 2 and 6 ethylene glycol units, and at least one ester of a fatty acid, especially of $C_{12}$-$C_{20}$, and of one or two glycerol groups, said fatty acid preferably comprising a $C_{12}$-$C_{20}$ alkyl chain which may be linear or branched, and saturated or unsaturated, preferably linear and saturated, chosen, for example, from glyceryl stearate, glyceryl laurate, glyceryl myristate, polyglyceryl-2 stearate, polyglyceryl-2 laurate and polyglyceryl-2 myristate, preferably from glyceryl stearate, and a mixture thereof.

A composition according to the invention has a content of nonionic surfactant(s) with an HLB value, in the Griffin sense, at 25° C., of less than 8, greater than or equal to 5% by weight relative to the total weight of the composition, preferably between 8% and 20% by weight relative to the total weight of the composition.

Preferably, a composition in accordance with the invention is free of anionic surfactant(s).

Preferably, a composition in accordance with the invention is free of amphoteric surfactant(s).

Moreover, the surfactant system may comprise one or more co-surfactants chosen from fatty alcohols comprising from 10 to 26 carbon atoms, better still from 12 to 24 carbon atoms and even better still from 14 to 22 carbon atoms.

Lamellar Phase Lβ

The surfactant system in accordance with the invention organizes the aqueous phase in the form of a lamellar phase Lβ, or paracrystalline phase Lβ, or lamellar gel phase.

This composition is stable at a room temperature of 25° C., having a viscosity preferentially ranging from 5 to 50 Pa·s, measured at a room temperature of 25° C. using a Rheomat RM 100® rheometer.

The term "lamellar gel phase or paracrystalline phase Lβ" means a phase in which the surfactant molecules and/or more generally the molecules of amphiphilic compounds are organized in the form of bimolecular layers spaced apart by aqueous leaflets. Within the bimolecular layers, the molecules are distributed in a hexagonal geometry, their hydrocarbon-based chains are in a crystalline state and are oriented perpendicular to the plane of the bimolecular layers but have no specific orientation relative to each other in the plane of these layers.

The paracrystalline phases Lβ are metastable phases in which the fatty chains are in solid form and are arranged randomly relative to each other, unlike the micellar, hexagonal, cubic and lamellar fluid paracrystalline phases (Lα)

in which the fatty chains are in liquid form, and unlike the crystalline phases in which the fatty chains are in solid form and oriented in an ordered manner relative to each other. The paracrystalline phases Lβ are metastable and, in general, they have a tendency to evolve towards crystallization. Now, the Applicant has found a particular surfactant system that makes it possible to obtain a stable paracrystalline phase Lβ, and thus cosmetic compositions for coating keratin fibres, in particular the eyelashes, which are stable and comfortable to apply, having a curling effect, by using a particular system of surfactant type in particular contents.

To identify the lamellar gel phase or paracrystalline phase Lβ of the surfactant system present in the composition of the invention, use may be made of various techniques, and especially the technique of x-ray scattering.

Wide-angle X-ray scattering (WAXS)

X-ray diagrams were recorded by a Mar345 image plate detector (Maresearch, Norderstedt, Germany), mounted on a FR591 rotary anode X-ray generator (Brüker, Courtaboeuf, France), used at 50 kV and at 50 mA. The monochromatic CuKα radiation ($\lambda$=1.541 Å) was focused with a 350 μm focal spot at 320 mm by double reflection on an elliptic cross-section multilayer Montel mirror (Incoatec, Geesthacht, Germany). The beam was defined under vacuum by four motorized carbon-tungsten slits (JJ-Xray, Roskilde, Denmark) positioned in front of the mirror (500 μm). Four additional guard slits were placed at the focal point with a 220 mm slit separation. The flux after the output mica windows was $3\times10^8$ photons/s. A 2-mm diameter circular metal wire beam stop was placed in air at 150 mm after the sample, and the detector was positioned at 360 mm. The X-ray diagrams were therefore recorded for a range of reciprocal spacing $q=4\pi^*\sin\theta/\lambda$ of 0.03-1.8 Å$^{-1}$, in which 0 is the scattering angle. The repetitive distances $d=2\pi/q$ should be between 200 Å and 3.5 Å. The samples were placed in 1.2-1.3 mm glass capillaries (Glas W. Müller, Germany) and introduced into a home-made capillary holder accommodating up to 20 capillaries at controlled temperature.

Hydrophilic Polymer(s)

The composition according to the invention comprises at least one (poly)oxyalkylenated hydrophilic polymer.

In the present patent application, the term "hydrophilic polymer" means a water-soluble or water-dispersible polymer.

In the present patent application, the term "water-soluble or water-dispersible polymer" means a polymer which, when introduced into water at a concentration equal to 1%, gives a macroscopically homogeneous solution whose light transmittance, at a wavelength equal to 500 nm, through a sample 1 cm thick, is at least 10%.

These (poly)oxyalkylenated hydrophilic polymer(s) may have a film-forming property.

In the present patent application, the term "film-forming polymer" is intended to mean a polymer that is capable, by itself or in the presence of an auxiliary film-forming agent, of forming a macroscopically continuous deposit, and preferably a cohesive deposit, and even better still a deposit of which the cohesion and mechanical properties are such that said deposit can be isolated and manipulated individually, for example when said deposit is prepared by pouring onto a non-stick surface such as a Teflon-coated or silicone-coated surface.

A (poly)oxyalkylenated hydrophilic polymer in accordance with the invention has a weight-average molecular mass Mw ranging from 1500 to 500 000 g/mol.

It is understood that these (poly)oxyalkylenated hydrophilic polymer(s) in accordance with the invention are thus distinct from an aqueous dispersion of particles formed from one or more film-forming polymers, more conventionally known as (pseudo)latex.

A composition according to the invention comprises a total solids content of (poly)oxyalkylenated hydrophilic polymer(s) of greater than or equal to 1% by weight, preferably 3% by weight, more preferentially 5% by weight, even more preferentially 8% by weight and in particular strictly greater than 10% by weight, relative to the total weight of the composition.

A composition according to the invention preferably comprises a total solids content of (poly)oxyalkylenated hydrophilic polymer(s) ranging from 1% to 25% by weight, better still from 3% to 20% and even better still from 5% to 18% by weight, relative to the total weight of the composition.

Preferably, the (poly)oxyalkylenated hydrophilic polymer(s) in accordance with the invention are linear.

Preferably, the (poly)oxyalkylenated hydrophilic polymer(s) in accordance with the invention are chosen from statistical polymers, block copolymers, and a mixture thereof.

The term "block copolymer" means a polymer comprising at least two different blocks and preferably at least three different blocks.

The hydrophilic polymer(s) bearing a (poly)oxyalkylene unit are chosen from:
- (poly)oxyalkylenated homopolymers, in particular polyoxyalkylenated homopolymers, more particularly polyethylene glycol homopolymers,
  - (poly)oxyalkylenated copolymers, in particular (poly)propylene glycol/(poly)ethylene glycol copolymers, in particular polypropylene glycol/polyethylene glycol copolymers,
- (poly)oxyalkylenated block copolymers, in particular (poly)oxyalkylenated diblock or triblock copolymers, more particularly diblock or triblock copolymers of (poly)ethylene glycol and of (poly)propylene glycol, even more particularly diblock or triblock copolymers of polyethylene glycol and of polypropylene glycol, and a mixture thereof.

The polymers according to the invention preferably comprise from 35 to 10 000 oxyethylene units, in particular from 35 to 5000 oxyethylene units and even more preferentially from 40 to 2500 oxyethylene units.

Examples of polyethylene glycol homopolymers that may be mentioned include polyethylene glycol 75 OE (PEG-75) sold under the commercial reference Lipoxol 4000 Med Flakes by the company Sasol.

As polyethylene glycol (PEG) homopolymers and/or polypropylene glycol (PPG)/polyethylene glycol (PEG) copolymers, mention may be made of the Poloxamer products sold by the company BASF.

As block copolymers bearing a (poly)oxyalkylene unit, mention may be made especially of a block copolymer corresponding to the following formula:

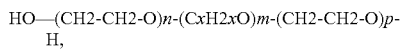
HO—(CH2-CH2-O)n-(CxH2xO)m-(CH2-CH2-O)p-H, in which formula n, m and p are, independently, integers ranging from 1 to 5000 and x is an integer strictly greater than 2 and less than or equal to 5.

In a preferred embodiment, n, m and p are integers ranging from 10 to 5000, such that n+m+p is between 35 and 10 000, or even between 35 and 5000 and better still between 40 and 2500.

The block copolymer(s) advantageously have a molecular weight of greater than or equal to 1500 g/mol, better still greater than 2000 g/mol and less than 500 000 g/mol.

As block copolymers bearing a (poly)oxyalkylene unit that may be used in the composition according to the invention, mention may be made of copolymers of propylene oxide and of ethylene oxide, also known as OE/OP polycondensates, more particularly OE/OP/OE triblock polycondensates.

Polyethylene glycol/polypropylene glycol/polyethylene glycol triblock polycondensates of the Poloxamer type are particularly preferred, for example those sold under the trade name Synperonic by the company Croda.

As hydrophilic polymers of the Poloxamer type, examples that may be mentioned include the following compounds:
  Poloxamer 124 sold under the trade name Synperonic PE/L 44 (11 OE/21 OP/11 OE) by the company Croda;
  Poloxamer 184 sold under the trade name Synperonic PE/L 64 (13 OE/30 OP/13 OE) of MW 2900 by the company Croda;
  Poloxamer 188 sold under the trade name Kolliphor P 188 or Pluracare/Pluronic F 68 Prill (75 OE/30 OP/75 OE) of MW 8350 by the company BASF;
  Poloxamer 338 sold under the trade name Synperonic PE/F 108 (128 OE/54 OP/128 OE) of MW 14 000 by the company Croda;
  Poloxamer 407 sold under the trade name Synperonic PE/F 27 (98 OE/67 OP/98 OE) of MW 12 000 by the company Croda.

The surfactant system and the hydrophilic polymer(s) bearing a (poly)oxyalkylene unit are present in a total respective weight content such that the weight ratio of the surfactant system to the hydrophilic polymer(s) ranges from 1 to 25 and more preferentially from 2 to 15.

Wax(es)

A composition according to the invention may comprise at least one wax.

More precisely, a composition according to the invention advantageously comprises from 0 to 25% by weight of wax(es), in particular from 1% to 15% by weight of wax(es), for example from 1% to 8% by weight, relative to the total weight of the composition.

A composition according to the invention may comprise a content of wax(es) of less than 8% by weight, in particular less than 3% by weight and better still less than 1% by weight relative to the total weight of the composition.

The wax(es) are generally a lipophilic compound that is solid at room temperature (25° C.), with a solid/liquid reversible change of state, having a melting point of greater than or equal to 30° C., which may be up to 200° C. and especially up to 120° C.

For the purposes of the invention, the melting point corresponds to the temperature of the most endothermic peak observed on thermal analysis (DSC) as described in standard ISO 11357-3; 1999. The melting point of the wax may be measured using a differential scanning calorimeter (DSC), for example the calorimeter sold under the name DSC Q2000 by the company TA Instruments.

Preferably, the waxes have a heat of fusion $\Delta Hf$ of greater than or equal to 70 J/g.

Preferably, the waxes comprise at least one crystallizable part, which is visible by X-ray observation.

The measurement protocol is as follows:

A 5 mg sample of wax placed in a crucible is subjected to a first temperature increase from −20° C. to 120° C., at a heating rate of 10° C./minute, and then is cooled from 120° C. to −20° C. at a cooling rate of 10° C./minute and finally subjected to a second temperature increase from −20° C. to 120° C. at a heating rate of 5° C./minute. During the second temperature increase, the following parameters are measured:

the melting point (Mp) of the wax, as mentioned previously corresponding to the temperature of the most endothermic peak of the melting curve observed, representing the variation of the difference in power absorbed as a function of the temperature, $\Delta Hf$: the heat of fusion of the wax, corresponding to the integral of the entire melting curve obtained. This heat of fusion of the wax is the amount of energy required to make the compound change from the solid state to the liquid state. It is expressed in J/g.

The wax(es) may be hydrocarbon-based waxes, fluoro waxes and/or silicone waxes and may be of plant, mineral, animal and/or synthetic origin.

A composition in accordance with the invention may comprise at least one hard wax chosen from the group consisting of polar waxes and apolar waxes, and a mixture thereof.

A composition in accordance with the invention may comprise at least one wax chosen from the group consisting of polar waxes and apolar waxes, and a mixture thereof.

A composition in accordance with the invention advantageously comprises at least one hard polar wax.

According to a particular embodiment, a composition according to the invention comprises less than 5% by weight of hard wax(es), which are preferably polar, and at least 3% by weight of (poly)oxyalkylenated hydrophilic polymer(s) relative to the total weight of the composition.

According to a particular embodiment, a composition according to the invention comprises at least 10% by weight of hard wax(es), which are preferably polar, and at least 1% by weight of (poly)oxyalkylenated hydrophilic polymer(s) relative to the total weight of the composition.

Hard Wax(es)

According to a particular embodiment of the invention, the composition advantageously comprises at least one hard wax.

For the purposes of the present invention, the term "hard wax" means a wax with a melting point greater than or equal to 65 to 120° C., more preferentially between 70 and 110° C. and even more preferentially between 75 and 100° C.

Advantageously, for the purposes of the present invention, the term "hard" wax means a wax having, at 20° C., a hardness of greater than 5 MPa, especially ranging from 5 to 30 MPa, preferably greater than 6 MPa and better still ranging from 6 to 25 MPa.

To take these hardness measurements, the wax is melted at a temperature equal to the melting point of the wax +20° C. To do this, 30 g of wax are placed in a 100 ml beaker 50 mm in diameter, which is itself placed on a magnetic-stirring hotplate.

An amount of about 15 g of molten wax is poured into a stainless-steel container 80 mm in diameter and 15 mm deep preheated to 45° C. in an oven. The wax is then left to recrystallize in a room thermostatically maintained at 20° C. for 24 hours before taking the measurement.

The mechanical properties of the wax or of the mixture of waxes are determined in a room thermostatically maintained at 20° C., using a texturometer sold under the name TA-XT2i by the company Swantech, equipped with a stainless-steel cylinder 2 mm in diameter.

The measurement comprises three steps: a first step after automatic detection of the surface of the sample, where the spindle moves at a measuring speed of 0.1 mm/s, and penetrates into the wax to a penetration depth of 0.3 mm, the software notes the maximum force value reached; a second "relaxation" step where the spindle remains at this position for one second and the force is noted after 1 second of relaxation; finally, a third "withdrawal" step in which the spindle returns to its initial position at a speed of 1 mm/s, and the probe withdrawal energy (negative force) is noted.

The hardness value corresponds to the maximum measured compression force in newtons divided by the area of the texturometer cylinder, expressed in mm², in contact with the wax. The hardness value obtained is expressed in megapascals or MPa.

As examples of hard wax, mention may be made especially of carnauba wax, candelilla wax, the wax Bis-PEG-12 Dimethicone Candelillate, for instance Siliconyl Candelilla Wax sold by the company Koster Keunen, hydrogenated jojoba wax, for instance the product sold by the company Desert Whale, hydrogenated palm oil such as the product sold by the company SIO, rice bran wax, sumach wax, ceresin waxes, laurel wax, Chinese insect wax, shellac wax, hydrogenated olive oil such as Waxolive from the company Soliance, the waxes obtained by hydrogenation of olive oil esterified with C12 to C18 fatty-chain alcohols, such as the products sold by the company Sophim under the trade names Phytowax Olive 12L44, 14L48, 16L55 and 18L57, the waxes obtained by hydrogenation of castor oil esterified with cetyl or behenyl alcohol, for instance the products sold under the names Phytowax Ricin 16L64 and Phytowax Ricin 22L73 by the company Sophim, hydrogenated camelina wax, ouricury wax, montan wax, ozokerite waxes, for instance Wax SP 1020 P sold by the company Strahl & Pitsch, microcrystalline waxes, for instance the product sold under the trade name Microwax HW by the company Paramelt, lauric, palmitic, cetylic and stearic acid triglycerides (INCI name: hydrogenated cocoyl glycerides), for instance the product sold under the trade name Softisan 100 by the company Sasol, polymethylene waxes, for instance the product sold under the trade name Cirebelle 303 by the company Sasol, polyethylene waxes, for instance the products sold under the trade names Performalene 400 polyethylene, Performalene 655 polyethylene and Performalene 500-L polyethylene by the company New Phase Technologies, alcohol-polyethylene waxes, for instance the product sold under the name Performacol 425 Alcohol by the company Bareco, the 95/5 ethylene/acrylic acid copolymer sold under the trade name wax AC 540 by the company Honeywell, hydroxyoctacosanyl hydroxystearate, for instance the product sold under the trade name Elfacos C 26 by the company Akzo, octacosanyl stearate, for instance the product sold under the name Kester Wax K 82 H by the company Koster Keunen, stearyl stearate, for instance the product sold under the name Liponate SS by the company Lipo Chemicals, pentaerythrityl distearate, for instance the product sold under the name Cutina PES by the company Cognis, the mixture of dibehenyl adipate, dioctadecyl adipate and dieicosanyl adipate (INCI name: $C_{18-22}$ dialkyl adipate), the mixture of dilauryl adipate and ditetradecyl adipate (INCI name: $C_{12-14}$ dialkyl adipate), the mixture of dioctadecyl sebacate, didocosyl sebacate and dieicosyl sebacate (INCI name: $C_{18-22}$ dialkyl sebacate), the mixture of dioctadecyl octadecanedioate, didocosyl octanedioate and dieicosyl octanedioate (INCI name: $C_{18-22}$ dialkyl octanedioate), for instance the products sold by the company Cognis, pentaerythrityl tetrastearate, for instance Liponate PS-4 from the company Lipo Chemicals, tetracontanyl stearate, for instance Kester Wax K76 H from the company Koster Keunen, stearyl benzoate, for instance Finsolv 116 from the company Finetex, behenyl fumarate, for instance Marrix 222 from the company Akzo Bernel, bis(1,1,1-trimethylolpropane) tetrastearate, for instance the product proposed under the name Hest 2T-4S by the company Heterene, didotriacontanyl distearate, for instance Kester Wax K82D from the company Koster Keunen, polyethylene glycol montanate containing 4 oxyethylene units (PEG-4), for instance the product sold under the trade name Clariant Licowax KST1, hexanediol disalicylate, for instance Betawax RX-13750 sold by the company CP Hall, dipentaerythrityl hexastearate, for instance the product proposed under the trade name Hest 2P-6S by the company Heterene, ditrimethylolpropane tetrabehenate, for instance the product sold under the trade name Hest 2T-4B by the company Heterene, jojoba esters, for instance the product sold under the trade name Floraester HIP by the company Floratech, mixtures of linear carboxylic acid (O20-40)/saturated hydrocarbons (INCI name: O20-40 acid polyethylene), for instance Performacid 350 acid from the company New Phase Technologies, synthetic wax of Fischer-Tropsch type, such as the product sold under the reference Rosswax 100 by the company Ross, stearyl alcohol, behenyl alcohol, dioctadecyl carbonate, for instance Cutina KE 3737, sucrose polybehenate, for instance Crodaderm B from the company Croda, and mixtures thereof.

Use may also be made of the waxes mentioned above in the form of commercially available mixtures, for example under the names Koster KPC-56 (mixture of 87.5% by weight of cetyl stearate, 7.5% by weight of behenyl alcohol and 5% by weight of palm kernel glycerides), KPC-60 (mixture of 87.5% by weight of stearyl stearate, 7.5% by weight of behenyl alcohol and 5% by weight of palm kernel glycerides), KPC-63 (mixture of 87.5% by weight of behenyl stearate, 7.5% by weight of behenyl alcohol and 5% by weight of palm kernel glycerides) and KPC-80 (mixture of 86% by weight of synthetic beeswax, 7.5% of hydrogenated plant oil and 6.5% by weight of behenyl alcohol) from the company Koster Keunen.

Use is preferably made of waxes of plant origin such as carnauba wax, candelilla wax, hydrogenated jojoba wax, sumach wax, the waxes obtained by hydrogenation of olive oil esterified with C12 to C18 fatty-chain alcohols sold by the company Sophim under the name Phytowax (12L44, 14L48, 16L55 and 18L57), rice bran wax, stearyl and behenyl alcohols, laurel wax or ouricury wax.

The hard wax(es) are preferably polar.

Polar Wax(es)

According to one embodiment, the composition according to the invention may comprise at least one polar wax.

For the purposes of the present invention, the term "polar wax" means a wax whose solubility parameter at 25° C., $\delta_a$, is other than 0 $(J/cm^3)^{1/2}$.

In particular, the term "polar wax" means a wax whose chemical structure is formed essentially from, or even constituted of, carbon and hydrogen atoms, and comprising at least one highly electronegative heteroatom such as an oxygen, nitrogen, silicon or phosphorus atom.

The definition and calculation of the solubility parameters in the Hansen three-dimensional solubility space are described in the article by C. M. Hansen: *The three-dimensional solubility parameters*, J. Paint Technol. 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a = (\delta_p^2 + \delta_h^2)^{1/2}$ The parameters $\delta_p$, $\delta_h$, $\delta_D$ and $\delta_a$ are expressed in $(J/cm^3)^{1/2}$.

The polar waxes may especially be hydrocarbon-based, fluoro or silicone waxes.

The term "silicone wax" means an oil comprising at least one silicon atom, especially comprising Si—O groups.

The term "hydrocarbon-based wax" is intended to mean a wax formed essentially from, or even constituted of, carbon and hydrogen atoms, and optionally oxygen and nitrogen atoms, and that does not contain any silicon or fluorine atoms. It may contain alcohol, ester, ether, carboxylic acid, amine and/or amide groups.

According to a first preferred embodiment, the polar wax is a hydrocarbon-based wax. As a hydrocarbon-based polar wax, a wax chosen from ester waxes and alcohol waxes is in particular preferred.

The expression "ester wax" is understood according to the invention to mean a wax comprising at least one ester function. The expression "alcohol wax" is understood according to the invention to mean a wax comprising at least one alcohol function, i.e. comprising at least one free hydroxyl (OH) group.

In particular, use may be made, preferably, as an ester wax, of those chosen from:

i) Waxes of formula $R_1COOR_2$ in which $R_1$ and $R_2$ represent linear, branched or cyclic aliphatic chains, the number of atoms of which varies from 10 to 50, which may contain a heteroatom such as 0, N or P and the melting point of which varies from 25° C. to 120° C. In particular, use may be made, as an ester wax, of a $C_{20}$-$C_{40}$ alkyl (hydroxystearyloxy) stearate (the alkyl group comprising from 20 to 40 carbon atoms), alone or as a mixture, or a $C_{20}$-$C_{40}$ alkyl stearate. Such waxes are especially sold under the names Kester Wax K 82 P®, Hydroxypolyester K 82 P®, Kester Wax K 80 P® and Kester Wax K82H by the company Koster Keunen. Use may also be made of a glycol and butylene glycol montanate (octacosanoate) such as the wax Licowax KPS Flakes (INCI name: glycol montanate) sold by the company Clariant.

ii) Bis(1,1,1-trimethylolpropane) tetrastearate, sold under the name Hest 2T-45® by the company Heterene, iii) Diester waxes of a dicarboxylic acid of general formula $R^3$—(—OCO—$R^4$—OCO—$R^5$), in which $R^3$ and $R^5$ are identical or different, preferably identical and represent a $C_4$-$C_{30}$ alkyl group (alkyl group comprising from 4 to 30 carbon atoms) and $R^4$ represents a linear or branched $C_4$-$C_{30}$ aliphatic group (alkyl group comprising from 4 to 30 carbon atoms) which may or may not contain one or more unsaturated groups, and preferably that is linear and unsaturated, iv) Mention may also be made of the waxes obtained by catalytic hydrogenation of animal or plant oils having linear or branched $C_8$-$C_{32}$ fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol, such as those sold under the names Phytowax ricin 16L64® and 22L73® by the company SOPHIM. Such waxes are described in patent application FR-A-2 792 190 and the waxes obtained by hydrogenation of olive oil esterified with stearyl alcohol such as the product sold under the name Phytowax Olive 18 L 57, or alternatively;

v) Beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumach wax; montan wax, orange wax, laurel wax and hydrogenated jojoba wax.

According to another embodiment, the polar wax may be an alcohol wax. According to the invention, the term "alcohol wax" means a wax comprising at least one alcohol function, i.e. comprising at least one free hydroxyl (OH) group.

Alcohol waxes that may be mentioned include for example the wax Performacol 550-L Alcohol from New Phase Technologies, stearyl alcohol and cetyl alcohol.

According to a second embodiment, the polar wax may be a silicone wax such as siliconized beeswax, or an alkyl dimethicone such as the $C_{30}$-$C_{45}$ alkyl dimethicone sold under the reference SF1642 by Momentive Performance Materials.

Preferably, the composition according to the invention comprises a content of polar wax, in particular a hard polar wax, and especially a polar hydrocarbon-based wax, ranging from 1% to 25% by weight of wax relative to the total weight of the composition, better still from 1% to 8% by weight and in particular from 1% to 5% by weight relative to the total weight of the composition.

Apolar Waxes:

The composition according to the invention may comprise at least one apolar wax.

For the purposes of the present invention, the term "apolar wax" means a wax whose solubility parameter at 25° C. as defined below, $\delta_a$, is equal to 0 $(J/cm^3)^{1/2}$.

Apolar waxes are in particular hydrocarbon-based waxes constituted solely of carbon and hydrogen atoms, and free of heteroatoms such as N, O, Si and P.

In particular, the expression "apolar wax" is understood to mean a wax that is constituted solely of apolar wax, rather than a mixture also comprising other types of waxes that are not apolar waxes.

As illustrations of apolar waxes that are suitable for the invention, mention may be made especially of hydrocarbon-based waxes, for instance microcrystalline waxes, paraffin waxes, ozokerite, polyethylene waxes, and a mixture thereof.

Polyethylene waxes that may be mentioned include Performalene 500-L Polyethylene and Performalene 400 Polyethylene sold by New Phase Technologies.

An ozokerite that may be mentioned is Ozokerite Wax SP 1020 P.

As microcrystalline waxes that may be used, mention may be made of Multiwax W 445® sold by the company Sonneborn, and Microwax HW® and Base Wax 30540® sold by the company Paramelt.

As microwaxes that may be used in the compositions according to the invention as apolar wax, mention may be made especially of polyethylene microwaxes such as those sold under the names Micropoly 200®, 220®, 220L® and 2505® by the company Micro Powders.

Dyestuffs

The compositions in accordance with the invention comprise at least one dyestuff.

This (or these) dyestuffs are preferably chosen from pulverulent substances, liposoluble dyes and water-soluble dyes, and mixtures thereof.

Preferably, the compositions according to the invention comprise at least one pulverulent dyestuff. The pulverulent dyestuffs may be chosen from pigments and nacres, and preferably from pigments.

The pigments may be white or coloured, mineral and/or organic, and coated or uncoated. Among the mineral pigments, mention may be made of metal oxides, in particular titanium dioxide, optionally surface-treated, zirconium, zinc or cerium oxide, and also iron, titanium or chromium oxide, manganese violet, ultramarine blue, chromium hydrate and ferric blue. Among the organic pigments that may be mentioned are carbon black, pigments of D&C type and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica in particular with ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

Preferably, the pigments contained in the compositions according to the invention are chosen from metal oxides.

These dyestuffs may be present in a content ranging from 0.01% to 30% by weight relative to the total weight of the composition and in particular from 3% to 22% by weight relative to the total weight of the composition.

Preferably, the dyestuff(s) are chosen from one or more metal oxides that are present in a content of greater than or equal to 2% by weight relative to the total weight of the composition, and advantageously inclusively between 3% and 22% by weight relative to the total weight of the composition.

Fillers

The compositions in accordance with the invention may also comprise at least one filler.

The fillers may be selected from those that are well known to those skilled in the art and commonly used in cosmetic compositions. The fillers may be mineral or organic, and lamellar or spherical. Mention may be made of talc, mica, silica, kaolin, polyamide powders, for instance the Nylon® sold under the name Orgasol® by the company Atochem, poly-β-alanine powders and polyethylene powders, powders of tetrafluoroethylene polymers, for instance Teflon®, lauroyllysine, starch, boron nitride, expanded polymeric hollow microspheres such as those of polyvinylidene chloride/acrylonitrile, for instance the products sold under the name Expancel® by the company Nobel Industrie, acrylic powders such as those sold under the name Polytrap® by the company Dow Corning, polymethyl methacrylate particles and silicone resin microbeads (for example Tospearls® from Toshiba), precipitated calcium carbonate, magnesium carbonate and magnesium hydrocarbonate, hydroxyapatite, hollow silica microspheres (Silica Beads® from Maprecos), glass or ceramic microcapsules, metal soaps derived from organic carboxylic acids having from 8 to 22 carbon atoms and in particular from 12 to 18 carbon atoms, for example zinc, magnesium or lithium stearate, zinc laurate and magnesium myristate.

The fillers may represent from 0.1% to 15% by weight and in particular from 0.5% to 10% by weight relative to the total weight of the composition.

Cosmetic Active Agents

The compositions in accordance with the invention may also comprise at least one cosmetic active agent.

As cosmetic active agents that may be used in the compositions in accordance with the invention, mention may be made especially of antioxidants, preserving agents, fragrances, neutralizers, emollients, coalescers, moisturizers, vitamins and screening agents, in particular sunscreens, and mixtures thereof.

Needless to say, a person skilled in the art will take care to select the optional additional ingredients and/or the amount thereof such that the advantageous properties of the composition according to the invention are not, or are not substantially, adversely affected by the envisaged addition.

Preferably, the composition according to the invention is a leave-in composition. Advantageously, the composition is a makeup composition and in particular a mascara.

Oil or Organic Solvent

The compositions according to the invention may comprise at least one oil or organic solvent.

The compositions according to the invention may in particular comprise at least one oil chosen from at least one non-volatile oil, at least one volatile oil, and a mixture thereof.

Non-Volatile Oil

The term "oil" means a fatty substance that is liquid at room temperature and at atmospheric pressure.

The term "non-volatile oil" means an oil that remains on the skin or the keratin fibre at room temperature and pressure. More precisely, a non-volatile oil has an evaporation rate strictly less than 0.01 mg/cm$^2$/min.

To measure this evaporation rate, 15 g of oil or of oil mixture to be tested are placed in a crystallizing dish 7 cm in diameter, which is placed on a balance in a large chamber of about 0.3 m$^3$ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

Said at least one non-volatile oil may be chosen from hydrocarbon-based oils and silicone oils, and mixtures thereof, preferably from hydrocarbon-based oils.

The non-volatile hydrocarbon-based oils that are suitable for the present invention may be chosen in particular from:

hydrocarbon-based oils of plant origin, such as triglycerides consisting of fatty acid esters of glycerol, the fatty acids of which may have chain lengths ranging from C4 to C28, these fatty acids possibly being linear or branched, and saturated or unsaturated; these oils are especially wheatgerm oil, sunflower oil, grapeseed oil, sesame seed oil, corn oil, apricot oil, castor oil, shea oil, avocado oil, olive oil, soybean oil, sweet almond oil, rapeseed oil, cottonseed oil, hazelnut oil, macadamia oil, jojoba oil, palm oil, alfalfa oil, poppy oil, pumpkin oil, sesame seed oil, marrow oil, rapeseed oil, blackcurrant oil, evening primrose oil, millet oil, barley oil, quinoa oil, rye oil, safflower oil, candlenut oil, passion flower oil and musk rose oil; or alternatively caprylic/capric acid triglycerides such as those sold by the company Stéarineries Dubois or those sold under the names Miglyol 810®, 812® and 818® by the company Sasol;

synthetic ethers containing from 10 to 40 carbon atoms;

linear or branched hydrocarbons of mineral or synthetic origin other than the polymers according to the invention, such as petroleum jelly, polybutenes, polydecenes and squalane, and mixtures thereof;

synthetic esters such as oils of formula R1COOR2 in which R1 represents a linear or branched fatty acid residue containing from 1 to 40 carbon atoms and R2 represents an especially branched hydrocarbon-based chain containing from 1 to 40 carbon atoms, on condition that R1+R2≥10, for instance purcellin oil (cetostearyl octanoate), isopropyl myristate, isopropyl palmitate, C12 to C15 alkyl benzoate, hexyl laurate, diisopropyl adipate, isononyl isononanoate, 2-ethylhexyl palmitate, isostearate isostearate, alkyl or polyalkyl octanoates, decanoates or ricinoleates such as propylene glycol dioctanoate; hydroxylated esters such as isostearate lactate and diisostearyl malate; and pentaerythritol esters;

fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol; and higher fatty acids such as oleic acid, linoleic acid or linolenic acid, and mixtures thereof.

The non-volatile silicone oils that are suitable for the present invention may be chosen in particular from:

the non-volatile silicone oils that may be used in the composition in accordance with the invention may be nonvolatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

A composition according to the invention optionally comprises at least one hydrocarbon-based non-volatile oil of plant origin, such as triglycerides consisting of fatty acid esters of glycerol the fatty acids of which may have chain lengths ranging from C4 to C28, in particular palm oil and hydrogenated jojoba oil(s). A composition according to the invention is preferably free of silicone non-volatile oil(s).

A composition according to the invention is preferably free of non-volatile oil. However, the total content of non-volatile oil(s) in a composition in accordance with the invention may range from 0.01% to 10% by weight, in particular less than 8% by weight and preferably less than 5% by weight relative to the total weight of the composition.

According to one preferred embodiment, a composition according to the invention comprises less than 3% by weight of non-volatile oil(s) relative to the total weight of the composition.

Volatile Oil

The composition according to the invention may comprise at least one volatile oil.

The term "volatile oil" means an oil (or non-aqueous medium) that can evaporate on contact with the skin in less than one hour, at room temperature and atmospheric pressure. The volatile oil is a cosmetic volatile oil, which is liquid at room temperature. More specifically, a volatile oil has an evaporation rate of between 0.01 and 200 mg/cm$^2$/min, limits included.

This volatile oil may be hydrocarbon-based.

The volatile hydrocarbon-based oil may be chosen from hydrocarbon-based oils containing from 7 to 16 carbon atoms.

The composition according to the invention may contain one or more volatile branched alkanes. The expression "one or more volatile branched alkanes" means, without preference, "one or more volatile branched alkane oils".

As a volatile hydrocarbon-based oil containing from 7 to 16 carbon atoms, mention may be made especially of C8-C16 branched alkanes, for instance C8-C16 isoalkanes (also known as isoparaffins), isododecane, isodecane, isohexadecane and for example the oils sold under the trade names Isopar or Permethyl, C8-C16 branched esters such as isohexyl neopentanoate, and mixtures thereof. Preferably, the volatile hydrocarbon-based oil containing from 8 to 16 carbon atoms is chosen from isododecane, isodecane and isohexadecane, and mixtures thereof, and is especially isododecane.

The composition according to the invention may contain one or more volatile linear alkanes. The term "one or more volatile linear alkanes" means, without preference, "one or more volatile linear alkane oils".

A volatile linear alkane that is suitable for the invention is liquid at room temperature (about 25° C.) and at atmospheric pressure (760 mmHg).

A "volatile linear alkane" that is suitable for the invention means a cosmetic linear alkane, which is capable of evaporating on contact with the skin in less than one hour, at room temperature (25° C.) and atmospheric pressure (760 mmHg, i.e. 101 325 Pa), which is liquid at room temperature, especially having an evaporation rate ranging from 0.01 to 15 mg/cm$^2$/min, at room temperature (25° C.) and atmospheric pressure (760 mmHg).

The linear alkanes, preferably of plant origin, comprise from 7 to 15 carbon atoms, in particular from 9 to 14 carbon atoms and more particularly from 11 to 13 carbon atoms.

As examples of linear alkanes that are suitable for use in the invention, mention may be made of the alkanes described in patent applications WO 2007/068 371 or WO 2008/155 059 by the company Cognis (mixtures of distinct alkanes that differ by at least one carbon). These alkanes are obtained from fatty alcohols, which are themselves obtained from coconut oil or palm oil.

As examples of linear alkanes that are suitable for the invention, mention may be made of n-heptane (C7), n-octane (C8), n-nonane (C9), n-decane (C10), n-undecane (C11), n-dodecane (C12), n-tridecane (C13), n-tetradecane (C14) and n-pentadecane (C15), and mixtures thereof, and in particular the mixture of n-undecane (C11) and n-tridecane (C13) described in Example 1 of patent application WO 2008/155 059 by the company Cognis. Mention may also be made of n-dodecane (C12) and n-tetradecane (C14) sold by Sasol under the references, respectively, Parafol 12-97 and Parafol 14-97, and also mixtures thereof.

The linear alkane may be used alone or as a mixture of at least two distinct alkanes that differ from each other by a carbon number of at least 1, and especially a mixture of at least two linear alkanes comprising from 10 to 14 distinct carbon atoms that differ from each other by a carbon number of at least 2, and in particular a mixture of C11/C13 volatile linear alkanes or a mixture of C12/C14 linear alkanes, in particular an n-undecane/n-tridecane mixture (such a mixture may be obtained according to Example 1 or Example 2 of WO 2008/155 059).

As a variant or additionally, the composition prepared may comprise at least one volatile silicone oil or solvent that is compatible with cosmetic use.

The term "silicone oil" means an oil containing at least one silicon atom, and especially containing Si—O groups. According to one embodiment, said composition comprises less than 10% by weight of volatile silicone oil(s), relative to the total weight of the composition, better still less than 5% by weight, or even is free of volatile silicone oil.

Volatile silicone oils that may be mentioned include cyclic polysiloxanes and linear polysiloxanes, and mixtures thereof. Volatile linear polysiloxanes that may be mentioned include hexamethyldisiloxane, octamethyltrisiloxane, decamethyltetrasiloxane, tetradecamethylhexasiloxane and hexadecamethylheptasiloxane. Volatile cyclic polysiloxanes that may be mentioned include hexamethylcyclotrisiloxane, octamethylcyclotetrasiloxane, decamethylcyclopentasiloxane and dodecamethylcyclohexasiloxane.

As a variant or additionally, the composition prepared may comprise at least one volatile fluoro oil.

The term "fluoro oil" means an oil containing at least one fluorine atom.

Volatile fluoro oils that may be mentioned include nonafluoromethoxybutane and perfluoromethylcyclopentane, and mixtures thereof.

A composition according to the invention is preferably free of volatile oil. However, at least one volatile oil may be present in a total content of less than 8% by weight. In particular, the volatile oil may be present in the composition in a content of less than 5% by weight relative to the total weight of the composition.

According to one preferred embodiment, a composition according to the invention comprises less than 3% by weight of volatile oil(s) relative to the total weight of the composition.

Assembly

An assembly for coating keratin fibres suitable for the invention may comprise an applicator suitable for applying said cosmetic composition for coating keratin fibres and, where appropriate, a packaging device suitable for receiving said composition. According to a particular embodiment, such an assembly may comprise means for heating a composition in accordance with the invention.

Heating Means

A composition in accordance with the invention may be subjected to heating means before and/or during application.

These heating means may be integrally fastened to an assembly for coating keratin fibres and more particularly to an applicator suitable for applying said cosmetic composition for coating keratin fibres, and optionally, where appropriate, to a packaging device suitable for receiving said composition.

These heating means are then suitable for melting at least part of the fatty phase, and especially at least part of the surfactant system and, where appropriate, at least part of the soft wax(es), and optionally at least part of the hard wax particles. The wax particles are heated to a temperature $T_c$ such that only part of the crystallizable chains is melted.

The heating means may also come into contact with or face the composition to be heated.

The composition may be heated while it is contained in a packaging device.

The composition may be heated while it is at least partially exposed to the ambient air.

The composition may be locally heated to a temperature greater than or equal to 45° C., even greater than or equal to 50° C., or even greater than or equal to 55° C. The temperature of the composition should not entail any risk of burning at the time of application. This is why when the composition is heated before application, a waiting time between the moment at which the composition is heated and the application to the keratin materials may optionally be necessary.

According to one embodiment variant, the composition is heated simultaneously with its application to the keratin fibres.

According to another variant, the composition is heated before and during its application to the keratin fibres.

The temperature to which at least part of the composition is heated may be inclusively between 45° C. and 95° C., better still 50° C. to 85° C. and even better still 55° C. to 75° C.

The temperature may be measured, for example, at the surface using an infrared pyrometer, for example a Fluke® brand machine.

The composition in accordance with the invention is capable of passing from a solid state to an at least partially liquid or even totally liquid state, and of doing so reversibly.

The solid/liquid change of state is at least partly due to the melting of a crystalline part, in particular of the wax(es) described previously in the present description.

The total heat of fusion of the composition is the heat consumed by the composition between −20° C. and 120° C. The total heat of fusion of the composition is equal to the area under the curve of the thermogram obtained using a differential scanning calorimeter (DSC), such as the calorimeter sold under the name MDSC 2920 by the company TA Instrument, with a temperature rise of 5° C. or 10° C. per minute, according to standard ISO 11357-3:1999.

Measuring Protocol:

A 5 mg sample of composition is placed in a crucible and subjected to a first temperature rise ranging from −20° C. to 120° C., at a heating rate of 10° C./minute, and is then cooled from 120° C. to −20° C. at a cooling rate of 10° C./minute. The sample is maintained at −20° C. for 5 minutes and finally subjected to a second temperature rise ranging from −20° C. to 100° C. at a heating rate of 5° C./minute.

During the second temperature rise, the variation in the difference in power absorbed by an empty crucible and by the crucible containing the sample of the composition is measured as a function of the temperature. The melting point of the compound is the value of the temperature corresponding to the top of the peak of the curve representing the variation in the difference in power absorbed as a function of the temperature.

The heat of fusion of the composition consumed at the temperature $T_c$ is the amount of energy required to make the compound pass from the solid or very viscous state at −20° C. to the state of the composition at the temperature $T_c$. It is expressed in J/g.

According to one embodiment of the invention, the composition is chosen such that the ratio of the heat consumed between −20° C. and $T_c$ by the product to the total heat consumed between −20° C. and 120° C. is greater than 0.4.

This relationship is confirmed, for example, for a temperature $T_c$ of the composition of between 45° C. and 80° C.

The choice of the temperature $T_c$ to which the composition is brought by the heating means may thus be made so that said ratio is greater than 0.4, for example inclusively between 0.4 and 0.9. In other words, heating is performed to a temperature such that the ratio of the heat supplied to heat the sample of composition to the temperature $T_c$ to the total heat is greater than or equal to 0.4, such a parameter being measured according to the DSC protocol described above.

Only the heated composition can come into contact with the keratin fibres, for example the eyelashes, during the application.

Applicator

The applicator may comprise means for smoothing and/or separating keratin fibres, such as the eyelashes or the eyebrows, in particular in the form of teeth, bristles or other reliefs.

The applicator is arranged to apply the composition to the eyelashes or the eyebrows, and may comprise, for example, a brush or a comb.

The applicator may also be used for finishing of the makeup, over a region of the eyelashes or eyebrows that is made up or laden with composition.

The brush may comprise a twisted core and bristles held between the turns of the core, or may be made in yet another way.

The comb is, for example, produced from a single part by moulding of a plastic.

In certain exemplary embodiments, the application member is mounted at the end of a wand, which wand may be flexible, which may contribute to improving the comfort during application.

Packaging Device

The packaging device may comprise a container for housing the composition for coating keratin fibres. This composition may then be withdrawn from the container by immersing the applicator therein.

This applicator may be firmly attached to a member for closing the container. This closing member may form a member for gripping the applicator. This gripping member may form a cap to be removably mounted on said container by any suitable means, such as screwing, click-fastening, coupling, etc. Such a container may thus reversibly house said applicator.

This container can be optionally equipped with a wiper suitable for removing a surplus of product withdrawn by the applicator.

A process for applying the composition according to the invention to the eyelashes or the eyebrows may also include the following steps:

forming a deposit of the cosmetic composition on the eyelashes or the eyebrows, leaving the deposit on the eyelashes or the eyebrows, it being possible for the deposit to dry.

It should be noted that, according to another embodiment, the applicator may form a product container. In such a case, a container may, for example, be provided for in the gripping member and an internal channel can internally connect this gripping member to the application members in relief.

Finally, it should be noted that the packaging and application assembly may be in the form of a kit, it being possible for the applicator and the packaging device to be housed separately in the same packaging article.

The examples above and that follow are given as illustrations of the present invention, and shall not limit the scope thereof.

EXAMPLES

Mascara composition C1, C2, C3 and C4 in accordance with the invention were prepared and evaluated:

| Phases | Ingredients with percentage content of solids | Commercial name | Suppliers | Mw in g/mol | C1 | C2 | C3 | C4 |
|---|---|---|---|---|---|---|---|---|
| Phase A | Steareth-2 | Brij S2-SO-(TH) | Croda | — | 10 | 10 | — | — |
| | Glyceryl stearate | Tegin M Pellets | Evonik Goldschmidt | — | — | — | 10 | — |
| | Steareth-20 | Brij S20-PA-(SG) | Croda | — | 20 | 20 | 20 | — |
| | Glyceryl stearate (and) PEG-100 stearate | Arlacel 165-FL-(CQ) | Croda | — | — | — | — | 30 |
| | Iron oxides | Sunpuro Black Iron Oxide C33-7001 | Sun | — | 8 | 8 | 8 | 8 |
| Phase B | Polyethylene glycol (75 OE) | Lipoxol 4000 Med Flakes | Sasol | 3000-3500 | 3 | — | 3 | 3 |
| | Poloxamer 188 | Pluracare/Pluronic F 68 Prill (USA) | BASF | 8400 | — | 3 | — | — |
| | | Water | | | qs 100 | qs 100 | qs 100 | qs 100 |
| Phase C | | Preserving agents | | | qs | qs | qs | qs |

1—Protocol for Preparing Said Compositions

Preparation of Phase A

The starting materials are first weighed out carefully using a balance (precision=0.01 g). The ingredients of phase A are melted in a jacketed heating pan in which circulates an oil whose temperature is controlled by means of a thermostatic oil bath. The nominal temperature is set at 80° C. After total melting, the pigment is introduced with stirring using a Rayneri blender. Stirring is continued until a homogeneous preparation is obtained.

Preparation of Phase B

The water is preheated in an electric kettle to 95° C. The polymer is introduced into the water in a beaker at a temperature of 80° C. with stirring using a Rayneri blender.

Mixing of Phases A and B

Phase B is poured into phase A with stirring for 5 minutes at 80° C. using a Rayneri blender. Phase A+B is then cooled to room temperature.

Addition of Phase C

Phase C is introduced into phase A+B when the temperature of the mixture is less than or equal to 40° C.

End of Formulation

The mascara thus obtained is transferred into a closed container to prevent it from drying out on contact with air. After 24 hours, the satisfactory nature of the homogeneity and the dispersion of the pigment are evaluated.

Comparative mascara compositions C'1, C'2 and C'3 outside the invention were prepared according to the same preparation protocol described above, and evaluated:

| Phases | Ingredients with percentage content of solids | Commercial name | Suppliers | Mw in g/mol | C'1 | C'2 | C'3 |
|---|---|---|---|---|---|---|---|
| Phase A | Steareth-2 | Brij S2-SO-(TH) | Croda | — | 10 | 10 | 10 |
| | Steareth-20 | Brij S20-PA-(SG) | Croda | — | 20 | 20 | 20 |
| | Iron oxides | Sunpuro Black Iron Oxide C33-7001 | Sun | — | 8 | 8 | 8 |
| Phase B | PEG-32 | Carbowax Sentry PEG 1450 FLNFFCC | Dow Chemical | 1300 | — | 3 | — |
| | Hydroxyethyl Cellulose | Cellosize QP 4400 H | Amerchol (Dow Chemical) | 730,000 | — | — | 3 |
| | | Water | | | qs 100 | qs 100 | qs 100 |
| Phase C | | Preserving agent | | | qs | qs | qs |

2—Composition Evaluation Method

The compositions prepared are evaluated regarding:
a) the black intensity, by visual observation and optionally quantification by measuring the parameter L* using a spectroradiometer such as a Minolta spectrocolorimeter, especially at 0°, in the L* a* b* system: the smaller the value of L*, the darker the colour.
b) the viscosity in Pa·s may be measured at 25° C. with a rheometer, for example a Rheomat rheometer,
c) the makeup result, and in particular:
the comfort on application by assessing the application properties in terms of the glidance and the playtime (redeposition, retouching), especially regarding the ease of allowing at least 20 brushstrokes on the eyelashes, better still at least 25 brushstrokes, or even at least 30 brushstrokes, without the user sensing any dragging,
the wear property of the curl via a rigidity study on a glass plate, consisting in spreading an amount of mascara and assessing the rigid feel.

3—Results of the Evaluation Measurements

| | C1 | C2 | C3 | C4 | C'1 | C'2 | C'3 |
|---|---|---|---|---|---|---|---|
| L* | 6.4 | 5.2 | 5.1 | 5.8 | 8.1 | 9.2 | 23.2 |
| Viscosity (Pa · s) | 7.1 | 7.8 | 7.1 | 8.6 | 1.2 | 1.3 | 30.2 |
| Rigidity | YES | YES | YES | YES | NO | NO | NO |

Compositions C1 to C4 according to the invention combine the desired properties, i.e.:
an intense black shade with a value L* of less than 10, while at the same time also having adequate rheology with a viscosity value at 25° C. of greater than 5 Pa·s to provide a satisfactory makeup result in terms of playtime and charging,
while at the same time affording good shaping and curling of the eyelashes, with a deposit that is rigid after drying.

The comparative reference compositions C'1 to C'3 are manifestly unsatisfactory in terms of shaping and curling of the eyelash fringe. Furthermore, compositions C'1 and C'2 have viscosities at 25° C. of less than 5 Pa·s. Furthermore, composition C'3 is manifestly less black than the compositions according to the invention.

It is understood that, in the context of the present invention, the weight percentages given for a compound or a family of compounds are always expressed as weight of solids of the compound in question.

Throughout the application, the wording "comprising one" or "including one" means "comprising at least one" or "including at least one", unless otherwise specified.

The invention claimed is:

1. A composition, comprising:
an aqueous phase representing from 30% to 80% by weight, relative to the total weight of the composition,
a lamellar phase Lβ formed by an aqueous phase-structuring surfactant system, said surfactant system comprising a content of surfactant(s) of greater than or equal to 15% by weight relative to the total weight of the composition, wherein the surfactant system comprises:
at least one nonionic surfactant with an HLB value at 25° C. of less than 8 selected from the group consisting of steareth-2, glyceryl stearate and a mixture thereof, and steareth-20,
wherein the nonionic surfactant with an HLB value at 25° C. of less than 8 and the steareth-20 are present in a total content of greater than or equal to 15% relative to the total weight of the composition, and
at least one (poly)oxyalkylenated hydrophilic polymer present in a content of greater than or equal to 1% by weight of solids relative to the total weight of the composition selected from the group consisting of polyethylene glycol homopolymer, (poly)propylene glycol/(poly) ethylene glycol copolymer, diblock or triblock copolymer of (poly)ethylene glycol and of (poly)propylene glycol, and a mixture thereof,
wherein the composition is free of anionic surfactants.

2. The composition of claim 1, wherein the steareth-20 is present in an amount of at least 7% by weight relative to the total weight of the composition.

3. The composition of claim 1, wherein the nonionic surfactant(s) of formula (I) with an HLB value at 25° C. of less than 8 are present in a content of greater than or equal to 8% by weight relative to the total weight of the composition.

4. The composition of claim 1, wherein the nonionic surfactant(s) with an HLB value at 25° C. of less than 8 and the steareth-20 are present in a total content ranging from 15% to 45% by weight relative to the total weight of the composition.

5. The composition of claim 1, wherein the nonionic surfactant(s) with an HLB value at 25° C. of less than 8 and the steareth-20 are present in a respective total content such that the weight ratio of the nonionic surfactant(s) with an HLB value at 25° C. of less than 8 to the steareth-20 ranges from 1/5 to 5.

6. The composition of claim 1, further comprising from 0 to 25% by weight of at least one wax relative to the total weight of the composition.

7. The composition of claim 1, comprising less than 5% by weight of wax and at least 3% by weight of the (poly) oxyalkylenated hydrophilic polymer(s) relative to the total weight of the composition.

8. The composition of claim 1, further comprising at least 10% by weight of at least one wax.

9. The composition of claim 1, further comprising at least one dyestuff comprising one or more pulverulent substance.

10. The composition of claim 1, wherein the composition has a value $L^*$ of less than 10 as determined using a spectroradiometer at 0° and the composition has a viscosity at 25° C. ranging from 5 to 50 Pa·s.

11. A process for coating keratin fibres, the process comprising applying the composition of claim 1 to keratin fibres.

* * * * *

UNITED STATES PATENT AND TRADEMARK OFFICE
CERTIFICATE OF CORRECTION

PATENT NO. : 10,493,015 B2  
APPLICATION NO. : 15/303181  
DATED : December 3, 2019  
INVENTOR(S) : Stephane Douezan et al.

Page 1 of 1

It is certified that error appears in the above-identified patent and that said Letters Patent is hereby corrected as shown below:

In the Claims

Column 30, Line 59, Claim 1, delete "glycol/(poly) ethylene" and insert -- glycol/(poly)ethylene --.

Signed and Sealed this
Sixteenth Day of June, 2020

Andrei Iancu
*Director of the United States Patent and Trademark Office*